US009006208B2

(12) United States Patent
Shichijo et al.

(10) Patent No.: US 9,006,208 B2
(45) Date of Patent: Apr. 14, 2015

(54) AGENT FOR TREATMENT OF DRY EYE CHARACTERIZED BY COMBINING P2Y$_2$ RECEPTOR AGONIST AND HYALURONIC ACID OR SALT THEREOF, METHOD FOR TREATING DRY EYE, AND USE OF THE P2Y$_2$ RECEPTOR AGONIST AND HYALURONIC ACID OR SALT THEREOF

(75) Inventors: Yuko Shichijo, Nara (JP); Atsuyoshi Dota, Nara (JP); Takashi Nagano, Nara (JP); Masatsugu Nakamura, Nara (JP); Asuka Sakamoto, Nara (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 3 days.

(21) Appl. No.: 13/821,717

(22) PCT Filed: Sep. 9, 2011

(86) PCT No.: PCT/JP2011/070578
§ 371 (c)(1),
(2), (4) Date: Mar. 8, 2013

(87) PCT Pub. No.: WO2012/033189
PCT Pub. Date: Mar. 15, 2012

(65) Prior Publication Data
US 2013/0172287 A1    Jul. 4, 2013

(30) Foreign Application Priority Data

Sep. 10, 2010   (JP) ................................. 2010-203198

(51) Int. Cl.
| | |
|---|---|
| *A01N 43/04* | (2006.01) |
| *A61K 31/70* | (2006.01) |
| *A61K 31/728* | (2006.01) |
| *A61K 31/675* | (2006.01) |
| *A61K 45/06* | (2006.01) |
| *A61K 31/7068* | (2006.01) |
| *A61K 31/7072* | (2006.01) |
| *A61K 31/7076* | (2006.01) |

(52) U.S. Cl.
CPC ............. *A61K 31/728* (2013.01); *A61K 31/675* (2013.01); *A61K 45/06* (2013.01); *A61K 31/7068* (2013.01); *A61K 31/7072* (2013.01); *A61K 31/7076* (2013.01)

(58) Field of Classification Search
None
See application file for complete search history.

(56) References Cited

U.S. PATENT DOCUMENTS

2005/0085439 A1    4/2005  Yerxa et al.
2008/0009463 A1*   1/2008  Yerxa et al. ..................... 514/51

FOREIGN PATENT DOCUMENTS

| | | |
|---|---|---|
| CN | 1250369 A | 4/2000 |
| CN | 1292795 A | 4/2001 |
| JP | 1-115902 A | 5/1989 |
| JP | 2001-504858 A | 4/2001 |
| JP | 2001-510484 A | 7/2001 |
| JP | 2001-526635 A | 12/2001 |
| WO | 98/34593 A1 | 8/1998 |
| WO | 98/34942 A2 | 8/1998 |
| WO | 99/05155 A2 | 2/1999 |

OTHER PUBLICATIONS

Office Action received for Chinese Patent Application No. 201180043577.5, mailed on Nov. 7, 2013, 8 pages (2 pages of English Translation and 6 pages of CNOA).
"Dictionary of Pharmaceutical Additives", 2007, p. 220, (Partial English Translation).
International Search Report and Written Opinion received for PCT Patent Application No. PCT/JP2011/070578, mailed on Nov. 1, 2011, 22 pages (11 pages of English Translation and 11 pages of Official Copy).
Brunschweiger et al., "P2 Receptors Activated by Uracil Nucleotides—An Update", Current Medicinal Chemistry, vol. 13, 2006, pp. 289-312.
Fujihara et al., "Improvement of Corneal Barrier Function by the P2Y2 Agonist INS365 in a Rat Dry Eye Model", Investigative Ophthalmology and Visual Science, vol. 42, No. 01, Jan. 2001, pp. 96-100.
Fujihara et al., "INS365 Suppresses Loss of Corneal Epithelial Integrity by Secretion of Mucin-Like Glycoprotein in a Rabbit Short-Term Dry Eye Mode", Journal of Ocular Pharmacology and Therapeutics, vol. 18, No. 4, 2002, pp. 363-370.
Fukuda et al., "Hyaluronate Sodium Tengan'eki no Baiyo Kato Kakumaku Saibo ni Taisuru Shogaisei", The Journal of Medicine, vol. 56, No. 3, 2006, pp. 385-388, (Partial English Translation).
Murakami et al., "Combined Effects of Hyaluronan and Artificial Tear Solution in Rat Dry Eye Model", Journal of the Eye, vol. 21, No. 1, 2004, pp. 87-90 (English Abstract submitted).
Murakami et al., "Novel Noninvasive Sensitive Determination of Tear Volume Changes in Normal Cats", Ophthalmic Research, vol. 34, 2002, pp. 371-374.
Murakami et al., "P2Y2 Receptor Stimulation Increases Tear Fluid Secretion in Rabbits", Current Eye Research, vol. 21, No. 4, 2000, pp. 782-787.
Nakamura et al., "Characterization of Water Retentive Properties of Hyaluronan", Cornea, vol. 12, No. 5, 1993, pp. 433-436.
Ng et al., "The Action of a Water-Soluble Carbodiimide on Adenosine-5'-Polyphosphates", Nucleic Acids Research, vol. 15, No. 8, 1987, pp. 3573-3580.
Pendergast et al., "Synthesis and P2Y Receptor Activity of a Series of Uridine Dinucleoside 5'-Polyphosphates", Bioorganic & Medicinal Chemistry Letters, vol. 11, 2001, pp. 157-160.
Tauber et al., "Double-Masked, Placebo-controlled Safety and Efficacy Trial of Diquafosol Tetrasodium (INS365) Ophthalmic Solution for the Treatment of Dry Eye", Investigative ophthalmology and visual science, vol. 44, Meeting Abstracts, 2003, p. 3738.

(Continued)

*Primary Examiner* — Patrick Lewis
(74) *Attorney, Agent, or Firm* — Morrison & Foerster LLP

(57) ABSTRACT

An agent for treatment of dry eye comprising a combination of a P2Y$_2$ receptor agonist at a therapeutically effective concentration and hyaluronic acid or a salt thereof at a therapeutically effective concentration, which agent has a dosage form of an ophthalmic agent, can promote the secretion of tear remarkably and can improve corneal epithelial disorders remarkably, and is therefore expected to be a novel agent for treatment of dry eye.

6 Claims, 2 Drawing Sheets

(56) References Cited

OTHER PUBLICATIONS

Tauber et al., "Double-Masked, Placebo-Controlled Safety and Efficacy Trial of Diquafosol Tetrasodium (INS365) Ophthalmic Solution for the Treatment of Dry Eye", Cornea, vol. 23, No. 8, 2004, pp. 784-792.

Yokoi, Norihiko, "Medical Treatment in Ophthalmology—Trends of 2008, Dry Eye", Journal of the Eye, vol. 25, No. 3, 2008, pp. 291-296, (Partial English Translation).

Yokoi et al., "Non-Invasive Methods of Assessing the Tear Film", Experimental Eye Research, vol. 78, 2004, pp. 399-407.

Yoshino et al., "Dry Eye Kanja O Taisho to shita Hyalein Tengan'eki to Tearbalance Tengan'eki no Hikaku Shiken", The Journal of Medicine, vol. 62, No. 1, 2009, pp. 101-110, (Partial English Translation).

Extended European Search Report and Search Opinion received for EP Patent Application No. 11823663.7, mailed on Jan. 28, 2014, 10 pages.

Aragona et al., "Long Term Treatment with Sodium Hyaluronate-Containing Artificial Tears Reduces Ocular Surface Damage in Patients with Dry Eye", British Journal of Ophthalmology, vol. 86, 2002, pp. 181-184.

Johnson et al., "Effectiveness of Sodium Hyaluronate Eyedrops in the Treatment of Dry Eye", Graefe's Archive for Clinical and Experimental Ophthalmology, vol. 244, 2006, pp. 109-112.

\* cited by examiner

AGENT FOR TREATMENT OF DRY EYE CHARACTERIZED BY COMBINING P2Y$_2$ RECEPTOR AGONIST AND HYALURONIC ACID OR SALT THEREOF, METHOD FOR TREATING DRY EYE, AND USE OF THE P2Y$_2$ RECEPTOR AGONIST AND HYALURONIC ACID OR SALT THEREOF

CROSS REFERENCE TO RELATED APPLICATIONS

This is a U.S. National Phase patent application of PCT/JP2011/070578, filed Sept. 9, 2011, which claims priority to Japanese Patent Application No. 2010-203198, filed Sept. 10, 2010, each of which is hereby incorporated by reference in the present disclosure in its entirety.

TECHNICAL FIELD

The present invention relates to an agent for treatment of dry eye characterized by comprising a combination of a P2Y$_2$ receptor agonist at a therapeutically effective concentration and hyaluronic acid or a salt thereof at a therapeutically effective concentration, wherein the dosage form is an ophthalmic agent. The present invention also relates to a method for treating dry eye using the P2Y$_2$ receptor agonist and hyaluronic acid or a salt thereof. The present invention also relates to a P2Y$_2$ receptor agonist and hyaluronic acid or a salt thereof for use in the treatment of dry eye. The present invention also relates to use of the P2Y$_2$ receptor agonist and hyaluronic acid or a salt thereof for manufacturing an agent for treatment of dry eye.

BACKGROUND ART

Dry eye is a disease which starts with unpleasant levels of symptoms of dryness of eyes and an uncomfortable feeling in eyes and greatly prevents people from performing daily activities when the disease is worsened. The number of dry eye patients is increasing yearly in association with the coming of an aging society and the increase in VDT (video display terminal) works with personal computers. It is believed that the estimated number of dry eye patients is greater than or equal to 10,000,000 in the United States and greater than or equal to 8,000,000 in Japan.

Although the clinical conditions of dry eye are not elucidated completely, it is considered that the decrease in the volume of tear on the corneal and the conjunctival, which is caused by the decrease in the secretion of tear, the acceleration of the evaporation of tear and the like, is the main pathogenesis of dry eye. That is, the dryness of the corneal and the conjunctival associated with the decrease in the volume of tear induces pathological symptoms and/or observations including an ocular discomfort, a feeling of dryness of eyes, a feeling of fatigue of eyes, hyperemia, and keratoconjunctival epithelial disorders. If these symptoms and/or observations progress, the abnormality in vision occurs ultimately. Therefore, it is quite important to treat dry eye properly at an early stage.

It is believed that the most desired matter for the treatment methods for dry eye is to promote the secretion of tear in a dry eye patient. However, no agent for treatment of dry eye having such an activity is known. Then, in the conventional dry eye treatment, the administration of an artificial tear solution ophthalmic solution, the suppression of the excretion of tear with a punctal plug or the like is generally selected.

As an agent for treatment of dry eye, an ophthalmic solution containing hyaluronic acid has been generally used. Although hyaluronic acid does not have a tear secretion promotion action, it is disclosed in Cornea, 12(5), 433-436 (1993) (NPL 1) that, when hyaluronic acid retains multiple water molecules thereof, the hyaluronic acid can exhibit an excellent water-retaining property. Although there are various theories about the mechanism of action of an ophthalmic solution containing hyaluronic acid for the treatment of dry eye, it is believed that the water-retaining property of hyaluronic acid can alleviate the drying of the cornea and the conjunctiva.

On the other hand, a P2Y$_2$ receptor is one of subtypes of a P2Y receptor that is a purine receptor and is believed to be deeply involved in the regulation of the secretion of a chloride ion or the like. A ligand for a P2Y receptor is considered as being a nucleotide in a living body, and it is described in Current Medicinal Chemistry, 13(3), 289-312 (2006) (NPL 2) that nucleotides typified by uridine-5'-triphosphate (UTP), adenosine-5'-triphosphate (ATP) and derivatives thereof, dinucleotides typified by P$^1$,P$^4$-bis(5'-uridyl)tetraphosphate (also called "diquafosol" or "INS-365") and the like can act as agonists for a P2Y$_2$ receptor.

In recent years, it was found that these P2Y$_2$ receptor agonists have an action of promoting the secretion of tear, and these P2Y$_2$ receptor agonists are drawing attention as novel agents for treatment of dry eye. For example, Current Eye Research, 21(4), 782-787 (2000) (NPL 3) discloses that UTP and ATP can promote the secretion of tear in rabbits, and therefore it is suggested that the secretion of tear can be promoted by stimulating a P2Y$_2$ receptor. In Cornea, 23(8), 784-792 (2004) (NPL 4), it is reported that an ophthalmic solution containing diquafosol promoted the secretion of tear and ameliorated keratoconjunctival epithelial disorders in clinical tests.

However, there are still some severe dry eye patients who cannot be treated satisfactorily with the above-mentioned agents for treatment of dry eye, and therefore the development of an agent for treatment of dry eye having a more potent tear secretion promotion action has been demanded.

In Japanese National Patent Publication No. 2001-504858 (PTL 1), it is suggested that hyaluronic acid can be added as an additive to a tear secretion promoter containing a compound capable of activating a purine receptor (P2Y$_2$ receptor). However, as mentioned in Dictionary of pharmaceutical additives, 220 (2007) (NPL 5), the largest amount of hyaluronic acid that can be used as an additive in an ophthalmic agent is 0.2 mg/g (0.02% (w/w)), and it is not described or suggested that a therapeutically effective concentration (no less than 0.1% (w/v) in terms of the concentration in an ophthalmic solution) of hyaluronic acid and a P2Y$_2$ receptor agonist are administered in combination.

As stated above, it is not found clearly as to what effect can be achieved when a P2Y$_2$ receptor agonist and a therapeutically effective concentration of hyaluronic acid are used in combination.

CITATION LIST

Patent Literature

PTL 1: Japanese National Patent Publication No. 2001-504858

Non Patent Literature

NPL 1: Cornea, 12(5), 433-436 (1993)
NPL 2: Current Medicinal Chemistry, 13(3), 289-312 (2006)

NPL 3: Current Eye Research, 21(4), 782-787 (2000)
NPL 4: Cornea, 23(8), 784-792 (2004)
NPL 5: Dictionary of pharmaceutical additives, 220 (2007)

SUMMARY OF INVENTION

Technical Problem

Thus, the search for a novel agent for treatment of dry eye having a more potent tear secretion promotion action is an interesting problem.

Solution to Problem

The present inventors have made intensive and extensive studies for the purpose of searching for a novel agent for treatment of dry eye. As a result, it was found that, when a P2Y$_2$ receptor agonist and a therapeutically effective concentration (0.1% and 0.3%) of hyaluronic acid or a salt thereof were administered in combination to the eyes of normal rabbits, remarkable promotion of the secretion of tear in the rabbits was observed. This finding led to the present invention. Further, when a P2Y$_2$ receptor agonist and hyaluronic acid or a salt thereof at a therapeutically effective concentration were administered in combination to eyes, a significant ameliorating effect on corneal epithelial disorders was observed in dry eye models.

Meanwhile, when a P2Y$_2$ receptor agonist and hyaluronic acid or a salt thereof at a concentration employed for the addition as an additive (0.002%) were administered in combination to eyes, the above-mentioned tear secretion promotion action was not observed. Referring to this result, the achievement of the above-mentioned effect is a marvelous result.

That is, the present invention provides an agent for treatment of dry eye (also referred to as a "present treatment agent", hereinbelow) characterized by comprising a combination of a P2Y$_2$ receptor agonist at a therapeutically effective concentration and hyaluronic acid or a salt thereof at a therapeutically effective concentration, wherein the dosage form is an ophthalmic agent.

The P2Y$_2$ receptor agonist in the agent for treatment of dry eye according to the present invention is preferably a compound represented by the following general formula [I] (also referred to as a "present compound" collectively, hereinbelow) or a salt thereof:

[Chemical formula 1]

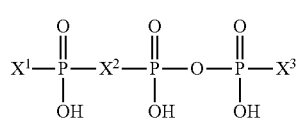

[wherein $X^1$ represents a hydroxy group, a thiol group, a group represented by the following formula:

[Chemical formula 2]

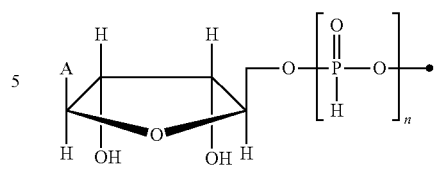

or a group represented by the following formula:

[Chemical formula 3]

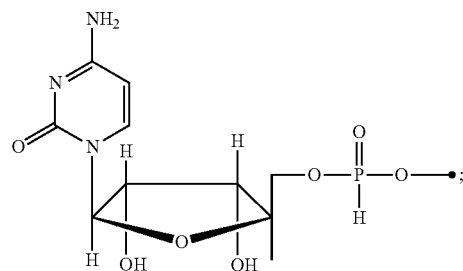

$X^2$ represents an oxygen atom, —NH— or —CR$^1$R$^2$—;
$X^3$ represents a group represented by the following formula:

[Chemical formula 4]

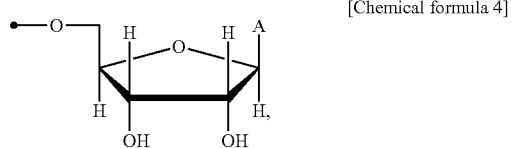

a group represented by the following formula:

[Chemical formula 5]

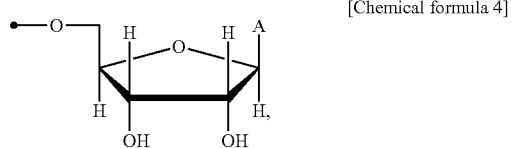

or a group represented by the following formula:

[Chemical formula 6]

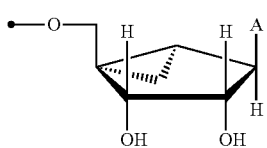

A represents a group represented by the following formula:

[Chemical formula 7]

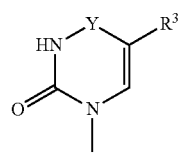

or a group represented by the following formula:

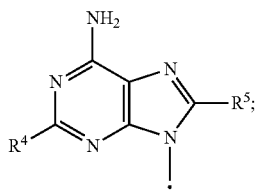

[Chemical formula 8]

Y represents CO, CS or $CHSR^6$;
$R^1, R^2, R^3, R^4, R^5$ and $R^6$ are the same as or different from one another and independently represent a hydrogen atom, a halogen atom or an alkyl group; and
n represents an integer of 0 to 4].

The $P2Y_2$ receptor agonist in the agent for treatment of dry eye according to the present invention is preferably $P^1,P^4$-bis(5'-uridyl)tetraphosphate (also referred to as "diquafosol", hereinbelow), uridine 5'-triphosphate (UTP), adenosine 5'-triphosphate (ATP) or a salt thereof.

The dosage form of the agent for treatment of dry eye according to the present invention is preferably an ophthalmic solution or an ophthalmic ointment.

The present invention also provides an ophthalmic solution for treating dry eye, characterized by comprising a combination of diquafosol or a salt thereof at a concentration of 1 to 5% (w/v) and hyaluronic acid or a salt thereof at a concentration of 0.05 to 0.5% (w/v).

The present invention further provides an ophthalmic solution for treating dry eye, characterized by comprising a combination of diquafosol or a salt thereof at a concentration of 3% (w/v) and hyaluronic acid or a salt thereof at a concentration of 0.1 to 0.5% (w/v).

The present invention still further provides a method for treating dry eye, which comprises administering a $P2Y_2$ receptor agonist at a therapeutically effective concentration and hyaluronic acid or a salt thereof at a therapeutically effective concentration in combination to a patient in need thereof, wherein the dosage form is an ophthalmic agent.

Also in the method for treating dry eye according to the present invention, the $P2Y_2$ receptor agonist is preferably the above-mentioned present compound.

Also in the method for treating dry eye according to the present invention, the $P2Y_2$ receptor agonist is preferably $P^1,P^4$-bis(5'-uridyl)tetraphosphate, uridine 5'-triphosphate, adenosine 5'-triphosphate or a salt thereof.

Also in the method for treating dry eye according to the present invention, the ophthalmic agent is preferably an ophthalmic solution or an ophthalmic ointment.

The present invention also provides a method for treating dry eye, which involves administering $P^1,P^4$-bis(5'-uridyl)tetraphosphate or a salt thereof at a concentration of 1 to 5% (w/v) and hyaluronic acid or a salt thereof at a concentration of 0.05 to 0.5% (w/v) in combination to a patient, wherein the dosage form is an ophthalmic solution.

The present invention also provides a method for treating dry eye, which comprises administering $P^1,P^4$-bis(5'-uridyl)tetraphosphate or a salt thereof at a concentration of 3% (w/v) and hyaluronic acid or a salt thereof at a concentration of 0.1 to 0.5% (w/v) in combination to a patient in need thereof, wherein the dosage form is an ophthalmic solution.

The present invention also provides a $P2Y_2$ receptor agonist and hyaluronic acid or a salt thereof for use in the treatment of dry eye by administering the $P2Y_2$ receptor agonist at a therapeutically effective concentration and hyaluronic acid or a salt thereof at a therapeutically effective concentration in combination, wherein the dosage form is an ophthalmic agent.

Also in the $P2Y_2$ receptor agonist and hyaluronic acid or a salt thereof according to the present invention, it is preferred that the $P2Y_2$ receptor agonist is the above-mentioned present compound.

Also in the $P2Y_2$ receptor agonist and hyaluronic acid or a salt thereof according to the present invention, the $P2Y_2$ receptor agonist is preferably $P^1,P^4$-bis(5'-uridyl)tetraphosphate, uridine 5'-triphosphate, adenosine 5'-triphosphate or a salt thereof.

Also in the $P2Y_2$ receptor agonist and hyaluronic acid or a salt thereof according to the present invention, the ophthalmic agent is preferably an ophthalmic solution or an ophthalmic ointment.

The present invention also provides $P^1,P^4$-bis(5'-uridyl)tetraphosphate or a salt thereof and hyaluronic acid or a salt thereof for use in the treatment of dry eye by administering $P^1,P^4$-bis(5'-uridyl)tetraphosphate or a salt thereof at a concentration of 1 to 5% (w/v) and hyaluronic acid or a salt thereof at a concentration of 0.05 to 0.5% (w/v) in combination, wherein the dosage form is an ophthalmic solution.

The present invention also provides $P^1,P^4$-bis(5'-uridyl)tetraphosphate or a salt thereof and hyaluronic acid or a salt thereof for use in the treatment of dry eye by administering $P^1,P^4$-bis(5'-uridyl)tetraphosphate or a salt thereof at a concentration of 3% (w/v) and hyaluronic acid or a salt thereof at a concentration of 0.1 to 0.5% (w/v) in combination, wherein the dosage form is an ophthalmic solution.

The present invention also provides use of a $P2Y_2$ receptor agonist and hyaluronic acid or a salt thereof for the production of an agent for treatment of dry eye comprising the $P2Y_2$ receptor agonist at a therapeutically effective concentration and hyaluronic acid or a salt thereof at a therapeutically effective concentration, wherein the agent for treatment of dry eye has a dosage form of an ophthalmic agent.

Also in the use according to the present invention, the $P2Y_2$ receptor agonist is preferably the above-mentioned present compound.

Also in the use and the $P2Y_2$ receptor agonist and hyaluronic acid or a salt thereof according to the present invention, the $P2Y_2$ receptor agonist is preferably $P^1,P^4$-bis(5'-uridyl)tetraphosphate, uridine 5'-triphosphate, adenosine 5'-triphosphate or a salt thereof.

Also in the use according to the present invention, the ophthalmic agent is preferably an ophthalmic solution or an ophthalmic ointment.

The present invention also provides use of $P^1,P^4$-bis(5'-uridyl)tetraphosphate or a salt thereof and hyaluronic acid or a salt thereof for manufacturing an agent for treatment of dry eye comprising $P^1,P^4$-bis(5'-uridyl)tetraphosphate or a salt thereof at a concentration of 1 to 5% (w/v) and hyaluronic acid or a salt thereof at a concentration of 0.05 to 0.5% (w/v).

The present invention also provides use of $P^1,P^4$-bis(5'-uridyl)tetraphosphate or a salt thereof and hyaluronic acid or a salt thereof for manufacturing an agent for treatment of dry eye comprising $P^1,P^4$-bis(5'-uridyl)tetraphosphate or a salt thereof at a concentration of 3% (w/v) and hyaluronic acid or a salt thereof at a concentration of 0.1 to 0.5% (w/v).

Advantageous Effects of Invention

As mentioned below, the present treatment agent can promote the secretion of tear remarkably and can improve corneal epithelial disorders remarkably, and is therefore expected to be a novel agent for treatment of dry eye. In addition, a method for treating dry eye using a P2Y$_2$ receptor agonist and hyaluronic acid or a salt thereof, a P2Y$_2$ receptor agonist and hyaluronic acid or a salt thereof for use in the treatment of dry eye, and use of a P2Y$_2$ receptor agonist and hyaluronic acid or a salt thereof for manufacturing an agent for treatment of dry eye are provided.

DESCRIPTION OF EMBODIMENTS

Figure 1:
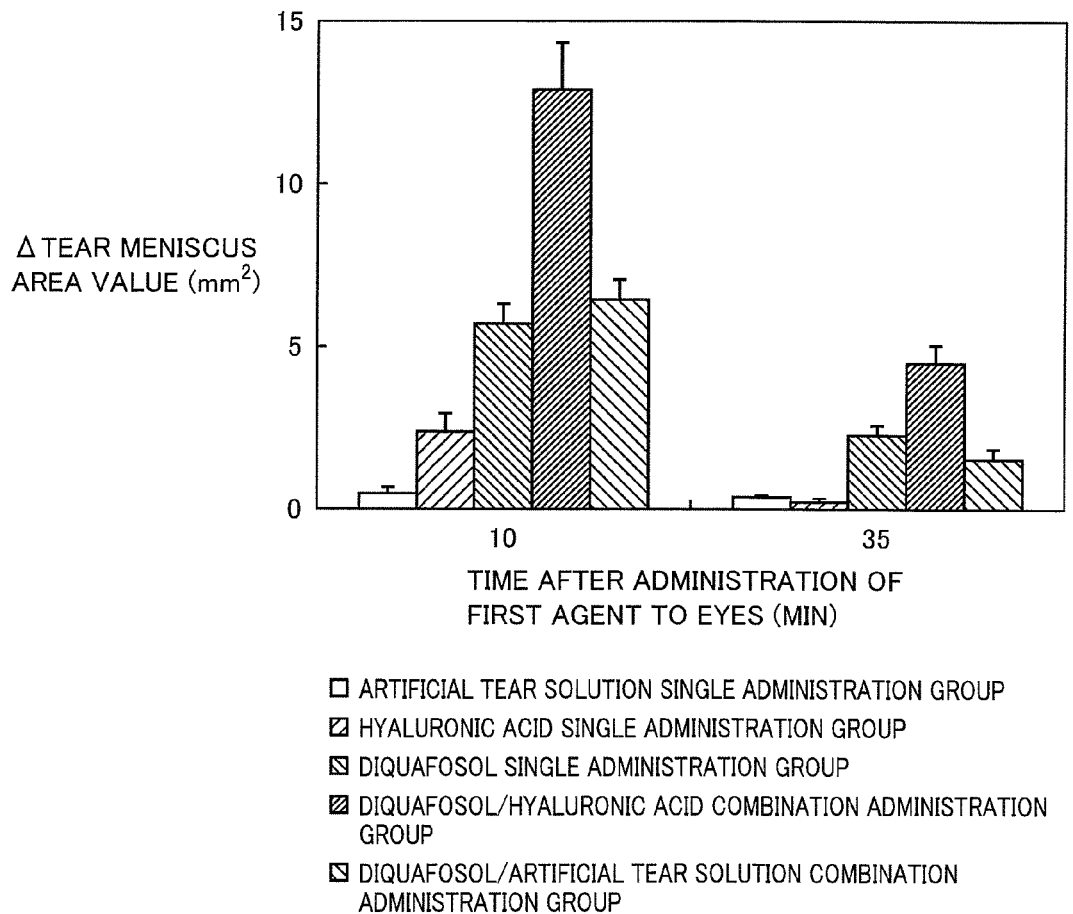
FIG. 1 is a graph illustrating the time course of a change in the tear meniscus area value after the administration of test drugs to eyes.

The agent for treatment of dry eye according to the present invention is greatly characterized by comprising a combination of a therapeutically effective concentration of a P2Y$_2$ receptor agonist and a therapeutically effective concentration of hyaluronic acid or a salt thereof. According to the present invention, a method for treating dry eye using a P2Y$_2$ receptor agonist and hyaluronic acid or a salt thereof in combination, a P2Y$_2$ receptor agonist and hyaluronic acid or a salt thereof for use in the treatment of dry eye, and use of a P2Y$_2$ receptor agonist and hyaluronic acid or a salt thereof for manufacturing an agent for treatment of dry eye are also provided.

The "P2Y$_2$ receptor agonist" in the present invention is not particularly limited, and may be any compound as long as the compound can bind to a P2Y$_2$ receptor and can activate a signaling pathway downstream of the P2Y$_2$ receptor. The P2Y$_2$ receptor agonist can be screened readily in accordance with the method disclosed in Bioorg. Med. Chem. Lett. 11(2), 157-160 (2001) or the like.

As for the P2Y$_2$ receptor agonist according to the present invention, the present compound represented by the general formula [I] or a salt thereof is preferred. In the present compound, the halogen atom refers to a fluorine atom, a chlorine atom, a bromine atom or an iodine atom. In the present compound, the number of carbon atoms in the alkyl group is not particularly limited, and the alkyl group is preferably a linear or branched alkyl group having 1 to 6 carbon atoms, such as a methyl group, an ethyl group, a propyl group, a butyl group, a pentyl group, a hexyl group, an isopropyl group, an isobutyl group, an isopentyl group, an isohexyl group, a t-butyl group and a 3,3-dimethylbutyl group.

(a) One preferred example of the present compound is a compound represented by the general formula [I] wherein each group is as follows:

(a1) X$^1$ represents a group represented by the following formula:

[Chemical formula 9]

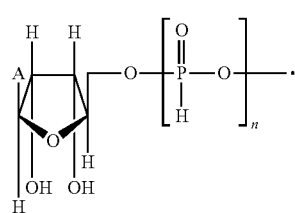

or a group represented by the following formula:

[Chemical formula 10]

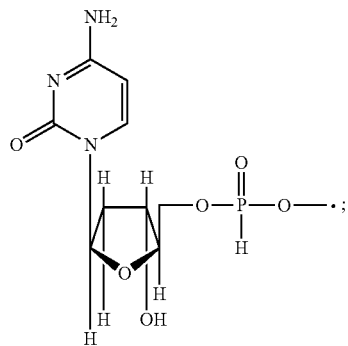

(a2) X$^2$ represents an oxygen atom;

(a3) X$^3$ represents a group represented by the following formula:

[Chemical formula 11]

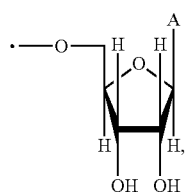

a group represented by the following formula:

[Chemical formula 12]

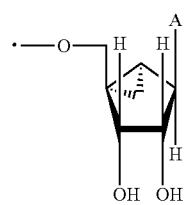

or a group represented by the following formula:

[Chemical formula 13]

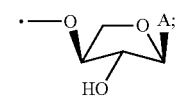

(a4) A represents a group represented by the following formula:

[Chemical formula 14]

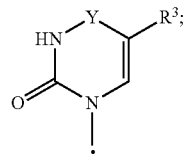

(a5) Y represents CO, CS or CHSR⁶;

(a6) $R^3$ and $R^6$ may be the same as or different from each other and independently represent a hydrogen atom, a halogen atom or an alkyl group; and (a7) n represents an integer of 0 to 4.

(b) Another preferred example of the present compound is a compound represented by the general formula [I] wherein each group is as follows:

(b1) $X^1$ represents a group represented by the following formula:

[Chemical formula 15]

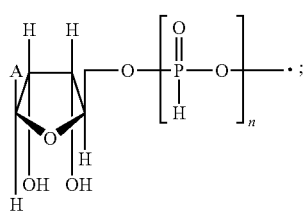

(b2) $X^2$ represents an oxygen atom;

(b3) $X^3$ represents a group represented by the following formula:

[Chemical formula 16]

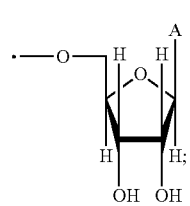

(b4) A represents a group represented by the following formula:

[Chemical formula 17]

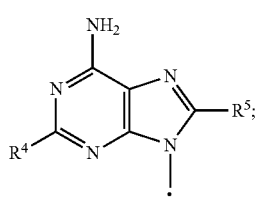

(b5) $R^4$ and $R^5$ may be the same as or different from each other and independently represent a hydrogen atom, a halogen atom or an alkyl group; and (b6) n represents 1.

(c) Still another preferred example of the present compound is a compound represented by the general formula [I] wherein each group is as follows:

(c1) $X^1$ represents a hydroxy group or a thiol group;

(c2) $X^2$ represents an oxygen atom, —NH— or —$CR^1R^2$—;

(c3) $X^3$ represents a group represented by the following formula:

[Chemical formula 18]

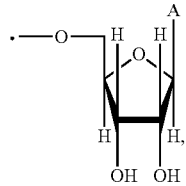

a group represented by the following formula:

[Chemical formula 19]

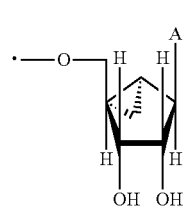

or a group represented by the following formula:

[Chemical formula 20]

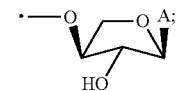

(a4) A represents a group represented by the following formula:

[Chemical formula 21]

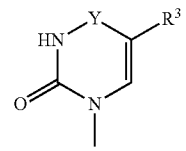

or a group represented by the following formula:

[Chemical formula 22]

(c5) Y represents CO, CS or CHSR⁶; and (c6) $R^1$, $R^2$, $R^3$, $R^4$, $R^5$ and $R^6$ are the same as or different from one another and independently represent a hydrogen atom, a halogen atom or an alkyl group.

Specific preferred examples of the present compound include the compounds mentioned below and salts thereof.

P¹,P³-bis(5'-uridyl)triphosphate [Up3U]
[Chemical formula 23]
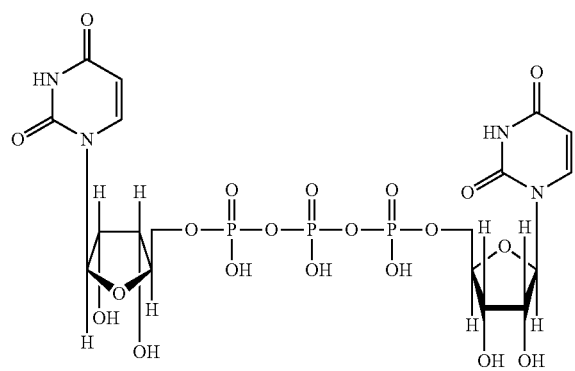
P¹,P⁴-bis(5'-uridyl)tetraphosphate [diquafosol]
[Chemical formula 24]
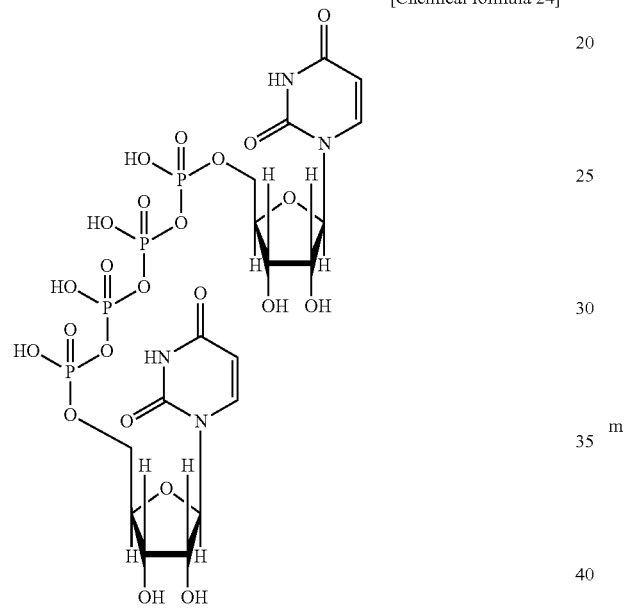
P¹-(uridine 5')—P⁴-(2'-deoxycytidine 5')tetraphosphate [Denufosol]
[Chemical formula 25]
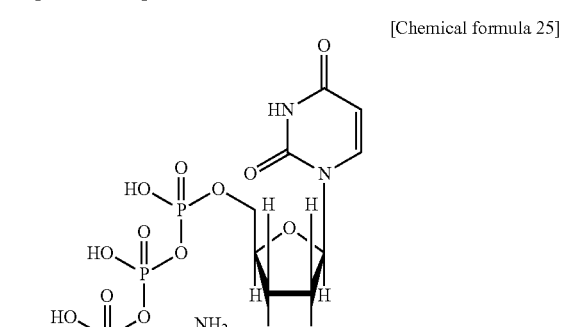
P¹,P⁵-bis(5'-uridyl)pentaphosphate [Up5U]
[Chemical formula 26]
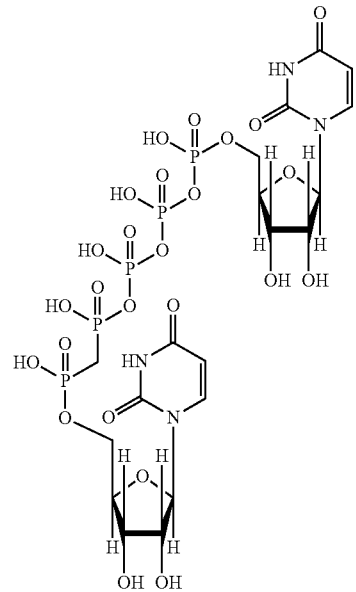
P¹,P⁶-bis(5'-uridyl)hexaphosphate [Up6U]
[Chemical Formula 27]
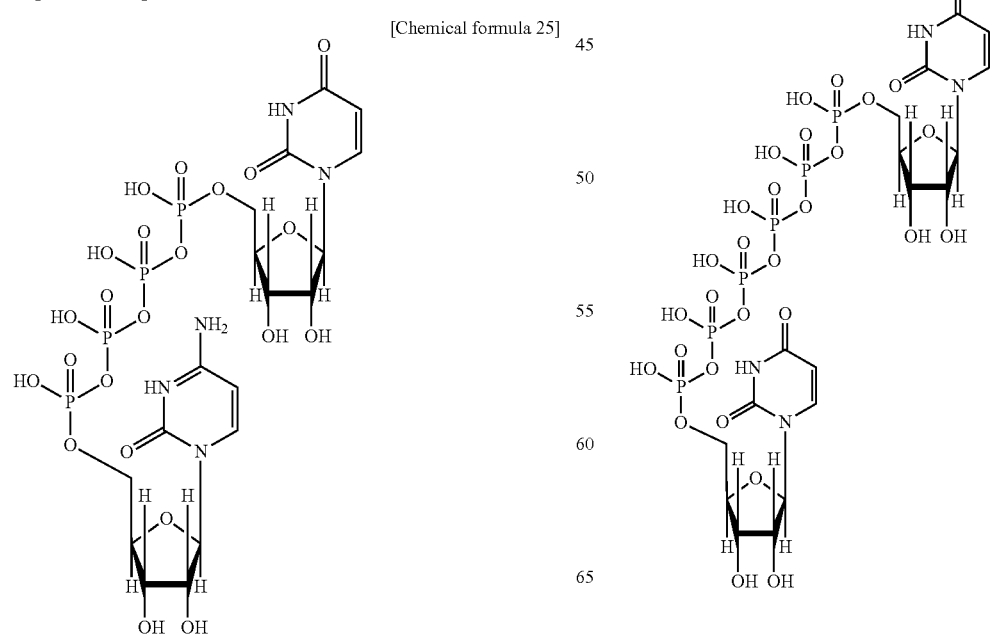

P¹,P⁷-bis(5'-uridyl)heptaphosphate [Up7U]

[Chemical Formula 28]

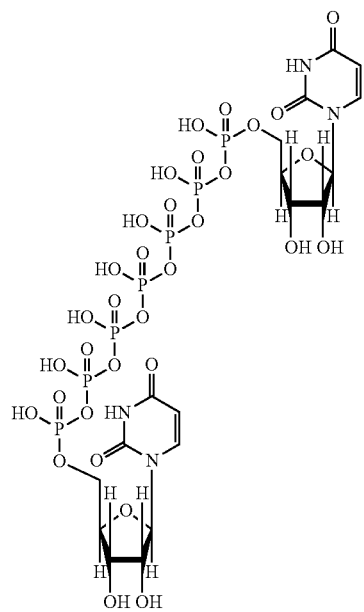

P¹,P⁴-bis(5'-adenosyl)tetraphosphate [Ap4A]

[Chemical Formula 29]

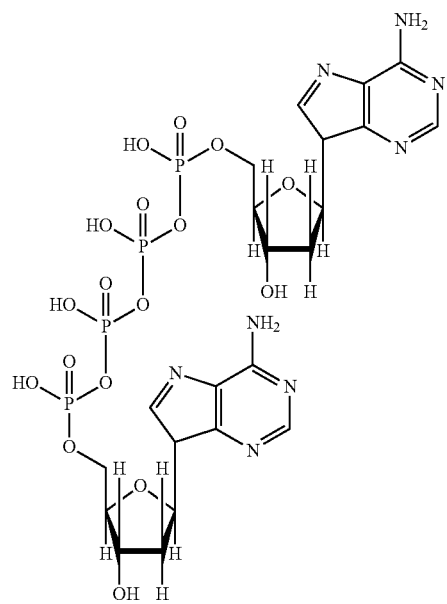

Uridine 5'-triphosphate [UTP]

[Chemical Formula 30]

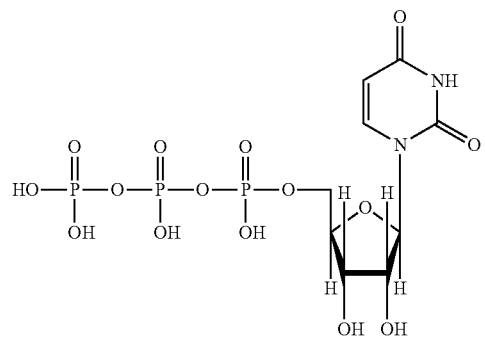

Uridine 5'-O-(3-thiotriphosphate) [UTPγS]

[Chemical Formula 31]

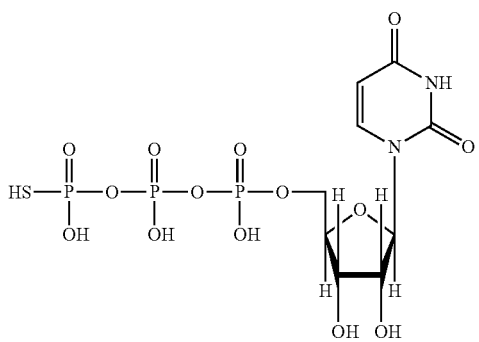

Uridine 5'-(β,γ-imide)triphosphate [β,γ-imide-UTP]

[Chemical Formula 32]

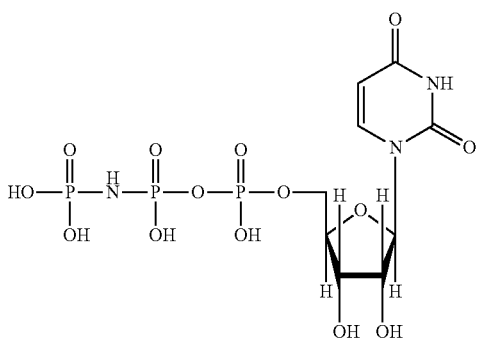

Uridine 5'-(β,γ-methylene)triphosphate [β,γ-methylene-UTP]

[Chemical Formula 33]

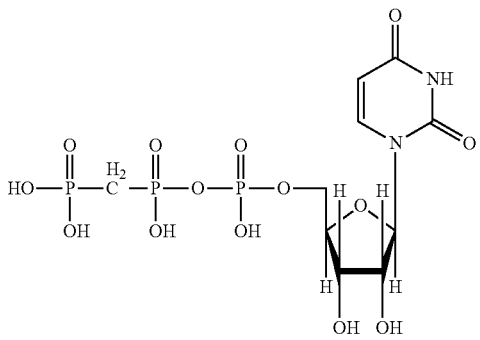

Uridine 5'-(β,γ-difluoromethylene)triphosphate [β,γ-difluoromethylene-UTP]

[Chemical Formula 34]

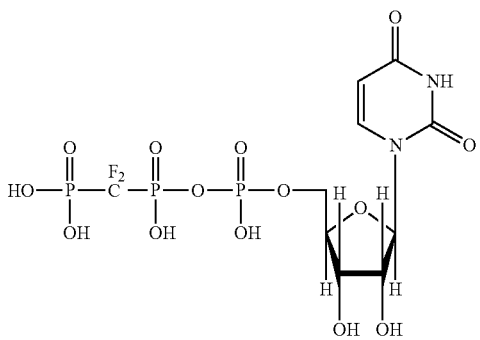

15

(N)-Methanocarba-UTP

[Chemical Formula 34]

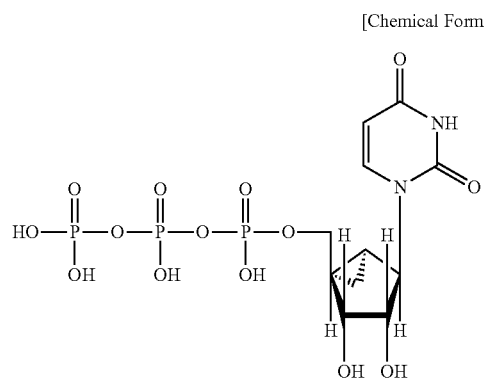

L-α-threofuranosyl-UTP [MRS-2488]

[Chemical formula 36]

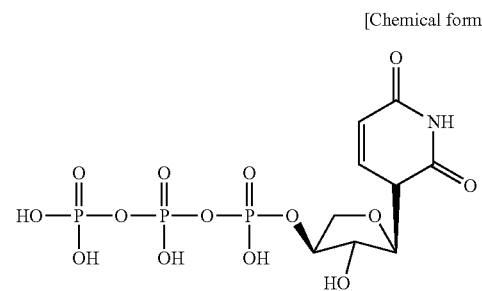

5-Bromouridine 5'-triphosphate [5-Br-UTP]

[Chemical formula 37]

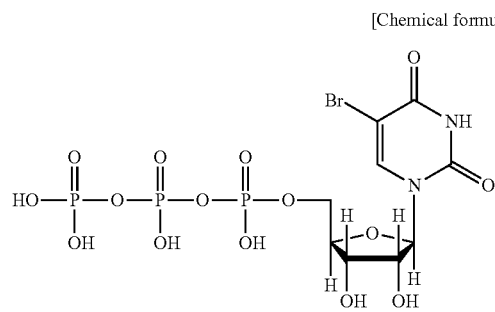

5-Ethyluridine 5'-triphosphate [5-ethyl-UTP]

[Chemical formula 38]

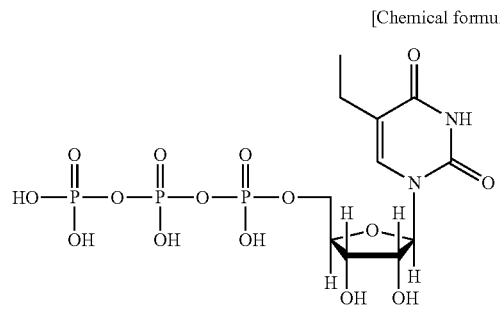

16

4-Thiouridine 5'-triphosphate [4-thio-UTP]
[Chemical Formula 39]

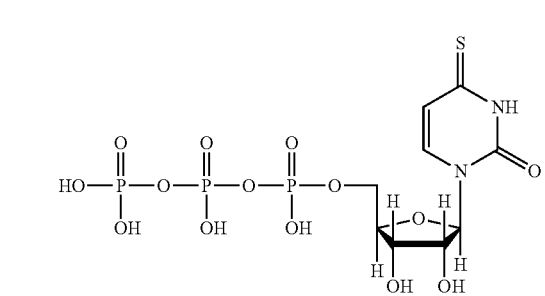

4-Hexylthiouridine 5'-triphosphate [4-hexylthio-UTP]

[Chemical formula 40]

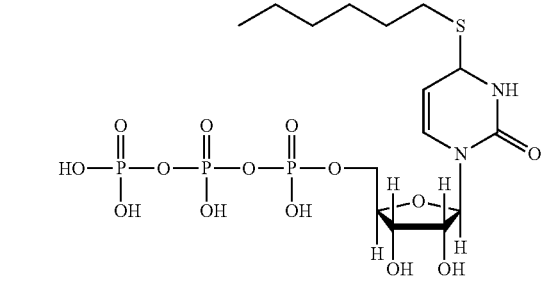

Adenosine 5'-triphosphate [ATP]

[Chemical formula 41]

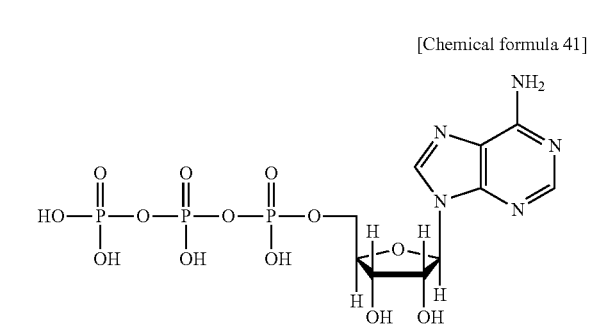

Adenosine 5'-O-(3-thiotriphosphate) [ATPγS]

[Chemical formula 42]

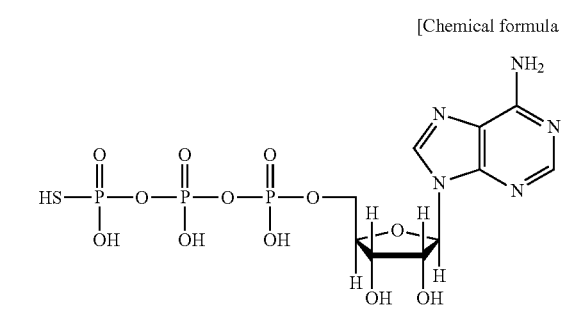

Adenosine 5'-(β,γ-imide)triphosphate [(β,γ-imido-ATP]

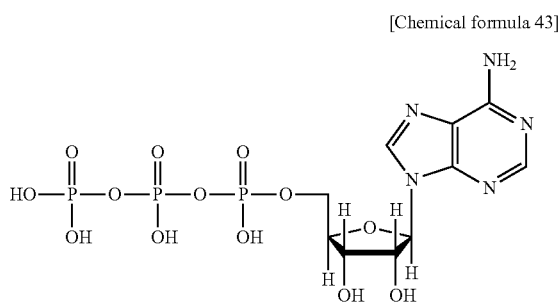

(N)-Methanocarba-ATP

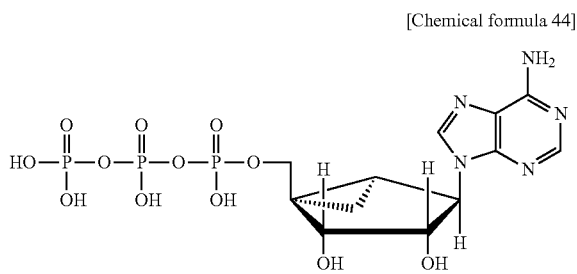

2-Chloroadenosine 5'-triphosphate [2-chloro-ATP]

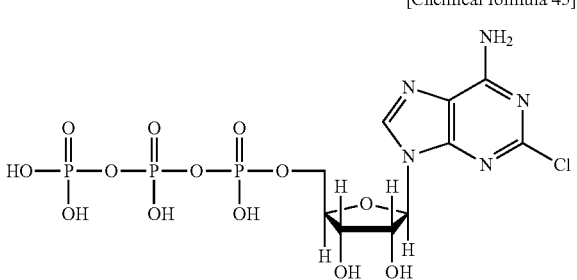

8-Bromoadenosine 5'-triphosphate [8-bromo-ATP]

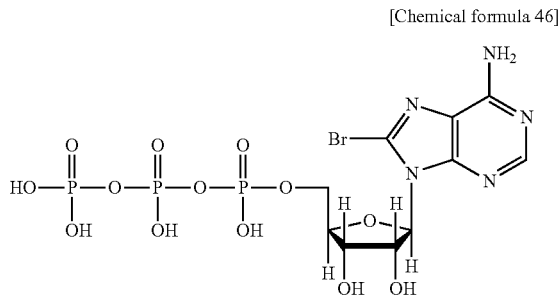

A compound which is particularly preferred as the $P2Y_2$ receptor agonist according to the present invention is diquafosol, UTP, ATP or a salt thereof.

A compound which is most preferred as the $P2Y_2$ receptor agonist according to the present invention is diquafosol or a salt thereof.

The present compound can be produced in accordance with conventional methods which have been employed in the field of organic synthetic chemistry, such as the methods disclosed in Nucleic acids research, 15(8), 3573-3580 (1987) and Bioorg. Med. Chem. Lett. 11(2), 157-160 (2001). Alternatively, commercially available compounds, such as products manufactured and sold by Sigma, may be used as the present compound.

Among the examples of the present compounds, particularly diquafosol and a salt thereof can be produced by the method disclosed in Japanese National Patent Publication No. 2001-510484. A sodium salt of UTP (catalog No.: U6625), a sodium salt of ATP (catalog No.: A7699), a lithium salt of ATPγS (catalog No.: A1388) and the like are commercially available from Sigma.

Hyaluronic acid to be used in the agent for treatment of dry eye according to the present invention is a compound represented by the following general formula [II]:

[Chemical formula 47]

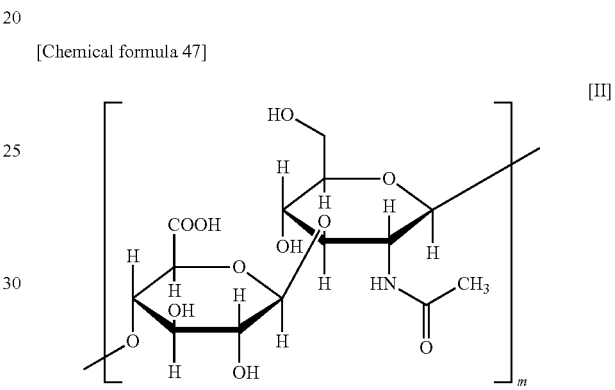

[wherein m represents a natural number].

"Hyaluronic acid" to be used in the present invention is preferably hyaluronic acid having an average molecular weight of 500,000 to 3,900,000, more preferably hyaluronic acid having an average molecular weight of 500,000 to 1,200,000.

The salt of the present compound or hyaluronic acid is not particularly limited, as long as the salt is a pharmaceutically acceptable salt. Examples of the salt include: salts with inorganic acids such as hydrochloric acid, hydrobromic acid, hydroiodic acid, nitric acid, sulfuric acid and phosphoric acid; salts with organic acids such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, sulfuric acid lauryl ester, methyl sulfate, naphthalenesulfonic acid and sulfosalicylic acid; quaternary ammonium salts with methyl bromide and methyl iodide; salts with halogen ions such as a bromine ion, a chlorine ion and an iodine ion; salts with alkali metals such as lithium, sodium and potassium; salts with alkali earth metals such as calcium and magnesium; metals salts with iron, zinc and the like; salts with ammonia; and salts with organic amines such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine and N,N-bis(phenylmethyl)-1,2-ethanediamine.

As the salts of the present compound or hyaluronic acid, sodium salts are preferred. Particularly, when the present compound is diquafosol, a tetrasodium salt of diquafosol which is represented by the following formula (simply referred to as "diquafosol sodium", hereinbelow) is preferred.

[Chemical formula 48]

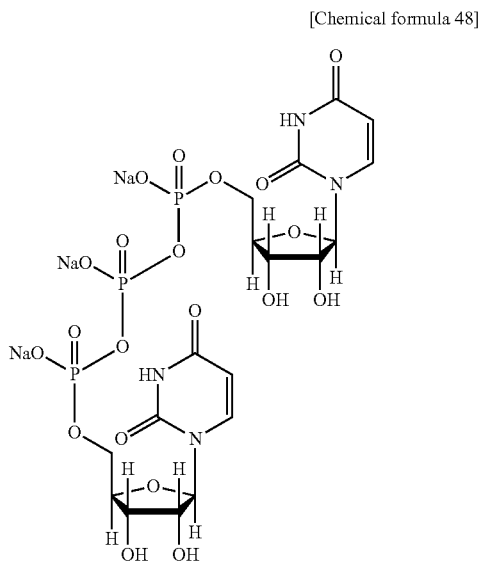

As the sodium salt of hyaluronic acid, a sodium salt represented by the following general formula [III] (also referred to as "sodium hyaluronate", hereinbelow) is particularly preferred:

[Chemical formula 49]

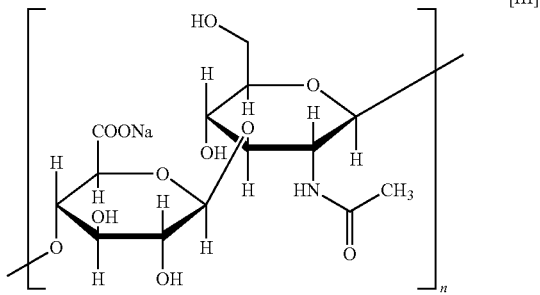

[wherein n represents a natural number].

The present compound, hyaluronic acid or a salt thereof may have the form of a hydrate or a solvate.

When the present compound or hyaluronic acid has a geometric isomer or an optical isomer, the isomer or a salt thereof is also included within the scope of the present invention. When the present compound or hyaluronic acid has a proton tautomer, the tautomer or a salt thereof is also included within the scope of the present invention.

When the present compound, hyaluronic acid or a salt thereof, a hydrate or a solvate has a crystal polymorphism or a crystal polymorphism group (a crystal polymorphism system), the crystal polymorphism and the crystal polymorphism group (the crystal polymorphism system) are also included within the scope of the present invention. The term "crystal polymorphism group (a crystal polymorphism system) as used herein refers to the individual crystal forms in the individual steps of changing the crystal forms and the whole of the process depending on the condition and state of production, crystallization, and preservation of the crystal (this state includes the formulated state).

Hyaluronic acid and a salt thereof can be produced in accordance with conventional methods employed in the field of organic synthetic chemistry, or can be produced in accordance with the method disclosed in Japanese Patent Laying-Open No. 1-115902. Hyaluronic acid and a salt thereof to be used in the present invention may be a commercially available product manufactured and sold by Sigma or the like. For example, a sodium salt of hyaluronic acid (catalog No.: H5388) is commercially available from Sigma.

In the present invention, the term "characterized by comprising a combination of a P2Y$_2$ receptor agonist at a therapeutically effective concentration and hyaluronic acid or a salt thereof at a therapeutically effective concentration" refers to a matter that a mixed ophthalmic agent comprising a P2Y$_2$ receptor agonist at a therapeutically effective concentration and hyaluronic acid or a salt thereof at a therapeutically effective concentration is administered at one time, and also refers to a matter that an ophthalmic agent comprising a P2Y$_2$ receptor agonist at a therapeutically effective concentration and an ophthalmic agent comprising hyaluronic acid or a salt thereof at a therapeutically effective concentration are administered separately and sequentially.

In the present invention, the term "therapeutically effective concentration" refers to a concentration at which a medicinal agent exhibits the pharmacological action thereof in an eye when the medicinal agent is topically administered to the eye.

In the present invention, the specific "therapeutically effective concentration" of the P2Y$_2$ receptor agonist may vary depending on the types of the compounds to be selected as the P2Y$_2$ receptor agonist, the dosage forms of the present treatment agent or the like. For example, when the P2Y$_2$ receptor agonist is diquafosol or a salt thereof, the therapeutically effective concentration is 0.01 to 20% (w/v), preferably 0.3 to 10% (w/v), more preferably 1 to 5% (w/v) when an ophthalmic solution is selected as the dosage form, and is 0.01 to 20% (w/w), preferably 0.3 to 10% (w/w), more preferably 1 to 5% (w/w), still more preferably 3% (w/w) when an ophthalmic ointment is selected as the dosage form. When the P2Y$_2$ receptor agonist is UTP, ATP or a salt thereof, the therapeutically effective concentration is 0.01 to 30% (w/v), preferably 0.3 to 20% (w/v), more preferably 1 to 10% (w/v) when an ophthalmic solution is selected as the dosage form, and is 0.1 to 30% (w/w), preferably 0.3 to 20% (w/w), more preferably 1 to 10% (w/w), when an ophthalmic ointment is selected as the dosage form.

In the present invention, the specific "therapeutically effective concentration" of hyaluronic acid or a salt thereof is 0.05 to 5% (w/v), preferably 0.05 to 1% (w/v), more preferably 0.05 to 0.5% (w/v), still more preferably 0.1 to 0.5% (w/v) when an ophthalmic solution is selected as the dosage form, and is 0.05 to 10% (w/w), preferably 0.05 to 5% (w/w), more preferably 0.05 to 1% (w/w), still more preferably 0.1 to 0.5% (w/w) when an eye ointment is selected as the dosage form.

The concentrations of "diquafosol or a salt thereof", "UTP or a salt thereof", "ATP or a salt thereof" or "hyaluronic acid or a salt thereof" in the present invention may be the concentration of a free form or a salt of diquafosol, UTP, ATP or hyaluronic acid.

In the present invention, "dry eye" is defined as "a chronic disease occurring in tear and a corneal and conjunctival epithelial caused by various factors, which is accompanied by an ocular discomfort and visual disorder." The dry eye in the present invention includes keratoconjunctivitis sicca (KCS), and also includes both tear-deficient dry eye and evaporative dry eye.

Tear-deficient dry eye is classified into dry eye associated with Sjogren syndrome and non-Sjogren syndrome-type dry eye. Non-Sjogren syndrome-type dry eye includes: dry eye associated with a tear gland disease such as congenital alacrima, sarcoidosis, and graft versus host disease (GVHD) associated with bone marrow transplantation; dry eye associated with tear organ obstruction caused by ocular pemphigus, Stevens-Johnson syndrome, trachoma or the like; dry eye associated with the decrease in reflex tear secretion caused by diabetes, keratorefractive surgery (LASIK: laser(-assisted) in situ keratomileusis) or the like; and so on.

Evaporative dry eye includes dry eye associated with the decrease in an oily layer caused by meibomian gland dysfunction, blepharitis or the like; dry eye associated with incomplete winking or incomplete eyelid closure caused by exophthalmos, lagophthalmos or the like; dry eye associated with deterioration of the stability of tear induced by the wearing of contact lends; dry eye associated with the decrease in the secretion of mucin from a goblet cell; dry eye associated with VDT operations; and so on.

In the present invention, the term "treatment of dry eye" is defined as the improvement of all of pathological symptoms and/or observations associated with dry eye through the promotion of the secretion of tear or the like, and includes the improvement of subjective symptoms associated with dry eye, such as a feeling of dryness of eyes, an ocular discomfort, a feeling of fatigue in eyes, a feeling of heaviness, a photophobia feeling, eye pain and blurred vision (hazy vision), as well as the improvement of hyperemia associated with dry eye, keratoconjunctival epithelial disorders and so on.

The present treatment agent may be formulated into a mixed ophthalmic agent by mixing the $P2Y_2$ receptor agonist, hyaluronic acid or a salt thereof, and a pharmaceutically acceptable additive together and employing a generally used technique. Alternatively, a pharmaceutically acceptable additive may be added to the $P2Y_2$ receptor agonist or hyaluronic acid or a salt thereof, respectively, and the resultant mixtures may be formulated as single-entity ophthalmic agents using a generally used technique.

An ophthalmic solution comprising only diquafosol or a salt thereof as an active ingredient can be prepared in accordance with the method disclosed in Japanese National Patent Publication No. 2003-160491. In Japan, "DIQUAS® ophthalmic solution 3%", which contains only diquafosol sodium as an active ingredient at a concentration of 0.3% (w/v), is commercially available. In addition, in Japan, ophthalmic solutions containing only hyaluronic acid or a salt thereof as an active ingredient, such as "Hyalein® ophthalmic solution 0.1%", which contains only sodium hyaluronate as an active ingredient at a concentration of 0.1% (w/v), and "Hyalein®Mini ophthalmic solution 0.3%", which contains only sodium hyaluronate as an active ingredient at a concentration of 0.3% (w/v), are also commercially available.

In the present invention, the present treatment agent is administered topically to eyes. Examples of the mode of administration of the present treatment agent include ocular instillation (including topical administration to eyes in the form of an ophthalmic ointment), subconjunctival administration, administration to the conjunctival sac and for subtenon administration, and ocular instillation is particularly preferred.

In the present invention, the dosage form of the "ophthalmic agent" is not particularly limited, as long as the agent can be used for topical administration to eyes. Examples of the dosage form include an ophthalmic solution, an ophthalmic ointment, an injection, an adhesive patch, a gel, and an intercalating agent. Among these dosage forms, an ophthalmic solution or an eye ointment is preferred. The dosage forms can be prepared using conventional techniques that have been generally employed in the art. In addition to these preparations, the present treatment agent may be formulated into a preparation for intraocular implanting or a preparation that is modified so as to be suitable for a drug delivery system (DDS) such as a microsphere.

The ophthalmic solution can be prepared using additives which are properly selected from tonicity agents such as sodium chloride, potassium chloride and concentrated glycerin; buffering agents such as sodium phosphate, sodium acetate and epsilon-aminocaproic acid; surfactants such as polyoxyethylene sorbitan monooleate, polyoxyl 40 stearate and polyoxyethylene hydrogenated castor oil; stabilizing agents such as sodium citrate and sodium edetate; and preservative agents such as benzalkonium chloride and paraben as required. The pH value of the ophthalmic solution may be any one, as long as the pH value falls within the ophthalmically acceptable range, and is generally preferably 4 to 8.

The eye ointment can be prepared using a vehicle that has been used generally, such as white petrolatum and liquid paraffin.

The injection can be prepared using an additive that is properly selected from tonicity agents such as sodium chloride; buffering agents such as sodium phosphate; surfactants such as polyoxyethylene sorbitan monooleate; and thickening agents such as methyl cellulose as required.

The intercalating agent can be prepared by pulverizing and mixing a biodegradable polymer such as hydroxy propyl cellulose, hydroxy propyl methyl cellulose, a carboxyvinyl polymer or polyacrylic acid with the present compound and compressing and molding the resultant powder, wherein an excipient, a binder, a stabilizing agent, a pH adjusting agent or the like may be used, if necessary.

The preparation for intraocular implanting can be prepared using a biodegradable polymer such as polylactic acid, polyglycolic acid, a lactic acid-glycolic acid copolymer or hydroxy propyl cellulose.

In the present invention, the dose regimen of the present treatment agent may vary properly depending on the dosage form employed, the severity of the condition, age and body weight of a patient to which the present treatment agent is to be administered, the directions by a physician, and the like. For example, when an ophthalmic solution or an ophthalmic ointment is selected as the dosage form of the present treatment agent, the ophthalmic solution or the ophthalmic ointment can be administered topically to eyes in 1 to 10 divided doses per day, preferably 2 to 8 divided doses per day, more preferably 4 to 6 divided doses per day. The dosage regimen means the dosage regimen for a mixed ophthalmic preparation comprising the $P2Y_2$ receptor agonist at a therapeutically effective concentration and hyaluronic acid or a salt thereof at a therapeutically effective concentration, as well as the dosage regimen for a case in which an ophthalmic agent comprising the $P2Y_2$ receptor agonist at a therapeutically effective concentration and an ophthalmic agent comprising hyaluronic acid or a salt thereof at a therapeutically effective concentration are administered separately and sequentially.

Hereinbelow, the results of pharmacological tests and preparation examples are shown. However, these examples are included merely for aiding the understanding of the present invention and are not to be construed to limit the scope of the present invention.

EXAMPLES

[Pharmacological Test 1]

The change in the tear fluid volume can be evaluated by measuring the value of a tear meniscus area stained with a fluorescein solution (Exp. Eye. Res., 78(3), 399-407 (2004)). Then, the time course of a change in the tear meniscus area value after the sequential administration of diquafosol sodium, which is a $P2Y_2$ receptor agonist, and sodium hyaluronate to eyes was evaluated in accordance with the method of Murakami et al. (Ophthalmic Res., 34, 371-374 (2002)), using normal male white rabbits.

(Drug Preparation Method)

Diquafosol sodium (30 mg) was dissolved in a phosphate buffer solution, and potassium chloride, sodium chloride, benzalkonium chloride and a pH adjusting agent were added to the resultant solution to prepare an isotonic and neutral aqueous solution (1 mL), which was used as a 3% diquafosol sodium ophthalmic solution in this test. As an artificial tear solution, "Soft Santear, 0.1%" manufactured and sold by Santen Pharmaceutical Co., Ltd. was used. As a sodium hyaluronate ophthalmic solution, "Hyalein® ophthalmic solution 0.1%" manufactured and sold by Santen Pharmaceutical Co., Ltd. was used.

(Test Method and Drug Administration Method)

A 0.1% fluorescein solution (3 μL) was administered onto a tear meniscus of the lower eyelid of each of normal male white rabbits (40 eyes of 20 rabbits in total), and a photograph of the tear meniscus that was stained with fluorescein accumulated in the eyelid was taken. The area of the stained tear meniscus part in the photograph was calculated using image analysis software, and the resultant value was employed as a baseline. Subsequently, an artificial tear solution, a 3% diquafosol sodium ophthalmic solution and a 0.1% hyaluronic acid ophthalmic solution were administered as follows.

Artificial tear solution single administration group: the artificial tear solution (50 μL) was instilled into eyes once (eight eyes of four rabbits per group).
  Diquafosol single administration group: a 3% diquafosol sodium ophthalmic solution (50 μL) was instilled into eyes once (eight eyes of four rabbits per group).
  Hyaluronic acid single administration group: the 0.1% sodium hyaluronate ophthalmic solution (50 μL) was instilled into eyes once (eight eyes of four rabbits per group).
  Diquafosol/artificial tear solution combination administration group: Five minutes after the administration of the 3% diquafosol sodium ophthalmic solution (50 μL) to eyes, the artificial tear solution (50 μL) was instilled into eyes (eight eyes of four rabbits per group).
  Diquafosol/hyaluronic acid combination administration group: Five minutes after the instillation of the 3% diquafosol sodium ophthalmic solution (50 μL) into eyes, the 0.1% sodium hyaluronate ophthalmic solution (50 μL) was instilled into eyes (eight eyes of four rabbits per group).

With respect to the artificial tear solution single administration group, the diquafosol single administration group, and the hyaluronic acid single administration group, 10 minutes and 35 minutes after the administration, a 0.1% fluorescein solution (3 μL) was instilled onto a tear meniscus of the lower eyelid, and a photograph of the tear meniscus stained with fluorescein accumulated in the eyelid was taken. On the other hand, with respect to the diquafosol/the artificial tear solution combination administration group and the diquafosol/hyaluronic acid combination administration group, 10 minutes and 35 minutes after the administration of the first agent, the same procedure as for the groups each administered with a single agent was performed.

(Evaluation Method)

The change in the tear meniscus area before and after the administration of each of the drugs was calculated as "Δ tear meniscus area value". The Δ tear meniscus area value at each measurement value is shown in FIG. 1. In FIG. 1, each value is an average value±a standard error with respect to 8 examples.

(Results)

In the diquafosol single administration group, an increase in the tear meniscus area value was observed both 10 minutes and 35 minutes after the administration. On the contrary, in the hyaluronic acid single administration group, a slight increase was observed 10 minutes after the administration and an increase in tear meniscus area value was not observed 35 minutes after the administration. On the other hand, with respect to the diquafosol/hyaluronic acid combination administration group, an increase in tear meniscus area value to a greater extent than that in the diquafosol single administration group or the hyaluronic acid single administration group was observed both 10 minutes and 35 minutes after the administration (i.e., 5 minutes and 30 minutes after the administration of the second agent). With respect to the diquafosol/artificial tear solution combination administration group, only an almost equivalent level of increase in tear meniscus area value as that in the diquafosol single administration group was observed.

(Discussion)

As mentioned in the section "Background Art", hyaluronic acid does not have a tear secretion promotion action. Actually, the 0.1% hyaluronic acid ophthalmic solution did not increase the tear meniscus area value at all 35 minutes after the administration. Nevertheless, when the 3% diquafosol sodium ophthalmic solution and the 0.1% sodium hyaluronate ophthalmic solution were administered in combination, surprisingly, a large increase in tear meniscus area value was observed in a period between 10 minutes after the administration of the first agent and 35 minutes after the administration of the first agent compared with that achieved by the single administrations of each of the ophthalmic solutions. In other words, it is considered that, when the 3% diquafosol sodium ophthalmic solution and the 0.1% sodium hyaluronate ophthalmic solution are administered in combination, a remarkably larger level of promotion of tear secretion than sum total of those achieved by single administrations of each of the ophthalmic solutions, was observed. As stated above, it was suggested that a remarkable tear secretion promotion action can be achieved when a $P2Y_2$ receptor agonist at a therapeutically effective concentration and hyaluronic acid or a salt thereof at a therapeutically effective concentration are administered in combination.

[Pharmacological Test 2]

A rat model from which an exorbital lacrimal gland is excised therefrom has been generally used as a model for evaluating therapeutic effects on corneal epithelial disorders induced by dry eye, and has also been used as a model for evaluating therapeutic effects of $P2Y_2$ receptor agonists (Invest. Ophthalmol. Vis. Sci., 42(1), 96-100 (2001)). Using a dry eye model which is additionally applied airflow to the rat model, it was examined whether or not an improvement effect on corneal epithelial disorders could be achieved by the administration of a $P2Y_2$ receptor agonist at a therapeutically effective concentration and hyaluronic acid or a salt thereof at a therapeutically effective concentration in combination.

(Method for Producing Dry Eye Models)

Using a male SD rat, a rat model from which an exorbital lacrimal gland was excised therefrom was produced in accordance with the method by Fujihara et al. (Invest. Ophthalmol. Vis. Sci., 42(1), 96-100 (2001)). That is, somnopentyl was administered to the rat to give general anesthesia, an exorbital lacrimal gland was excised from the rat, and then airflow (for 8 weeks) was additionally applied to the rat to induce a corneal epithelial disorder.

(Drug Preparation Method)

In the same manner as in Pharmacological test 1, a 3% diquafosol sodium ophthalmic solution was prepared. "Soft Santear" manufactured and sold by Santen Pharmaceutical Co., Ltd. was used as an artificial tear solution, and "Hyalein® ophthalmic solution 0.1%" manufactured and sold by Santen Pharmaceutical Co., Ltd. was used as a "0.1% sodium hyaluronate ophthalmic solution".

(Test Method and Drug Administration Method)

To the rats for which a corneal epithelial disorder was induced, the artificial tear solution, the 3% diquafosol sodium ophthalmic solution and the 0.1% hyaluronic acid ophthalmic solution were administered in the following manner.

Artificial tear solution single administration group: the artificial tear solution (5 µL) was instilled into both eyes 6 times per day for 6 weeks (eight eyes of four rats per group).

Hyaluronic acid single administration group: the 0.1% sodium hyaluronate ophthalmic solution (5 µL) was instilled into both eyes 6 times per day for 6 weeks (eight eyes of four rats per group).

Diquafosol single administration group: the 3% diquafosol sodium ophthalmic solution (5 µL) was instilled into both eyes 6 times per day for 6 weeks (eight eyes of four rats per group).

Artificial tear solution/hyaluronic acid combination administration group: the artificial tear solution and the 0.1% sodium hyaluronate ophthalmic solution (5 µL, for each) were instilled into both eyes 6 times per day for 6 weeks (six eyes of three rats per group).

Diquafosol/hyaluronic acid combination administration group: the 3% diquafosol sodium ophthalmic solution and the 0.1% sodium hyaluronate ophthalmic solution were instilled into both eyes 6 times per day for 6 weeks (eight eyes of four rats per group).

Among the rats for which a corneal epithelial disorder was induced, those rats to which no drug was administered for 6 weeks were defined as a non-administered group (eight eyes of four rats per group).

Six weeks after the initiation of the instillation into eyes, an affected part of the cornea was stained with fluorescein, and the occurrence of the corneal epithelial disorder was determined in accordance with the method by Murakami et al. (Journal of the Eye (Atarashii Ganka), 21(1), 87-90 (2004)). That is, with respect to each of an upper part, an intermediate part and a lower part of the cornea, scores of the degree of staining with fluorescein were determined in accordance with the criteria mentioned below, and the average value of the sum total of the scores was calculated. In each of the scores 0, 1, 2 and 3, an intermediate value 0.5 was set.

(Determination Criteria)

0: not stained

1: sparsely stained, wherein dot-shaped stained parts were distanced from each other 2: the degree of staining was moderate, wherein some of dot-shaped stained parts were adjacent to each other 3: densely stained, wherein dot-shaped stained parts were adjacent to one another (Results)

Figure 2:
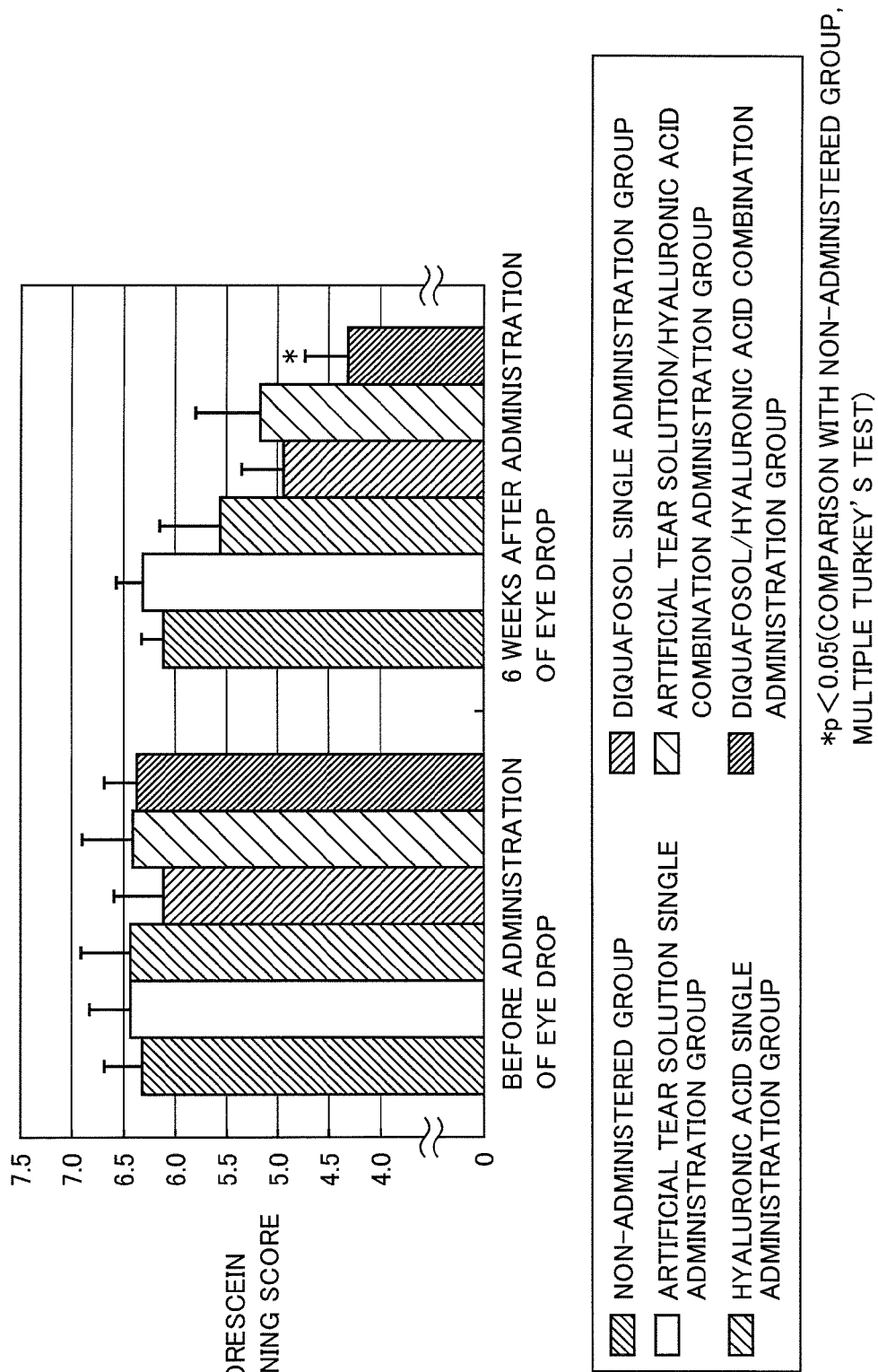
FIG. 2 is a graph illustrating a change in scores of the fluorescein staining of the cornea before and after the administration of test drugs to eyes.

A graph of calculated fluorescein staining scores for each group is shown in FIG. 2. In this graph, each of the scores is an average value±a standard error for 6 or 8 examples.

As apparent from FIG. 2, in the hyaluronic acid single administration group and the diquafosol single administration group, although the tendency of improvement in fluorescein staining scores was observed, the improvement that can be considered as being statistically significant was not observed. On the other hand, in the diquafosol/hyaluronic acid combination administration group, remarkable improvement in fluorescein staining scores was observed, wherein the improvement effect was statistically significant (p<0.05, multiple Tukey's test (when compared with the non-administered group)).

(Discussion)

As apparent from the above-mentioned results, it was demonstrated that a severe corneal epithelial disorder that cannot be treated by the single administration of each of the ophthalmic solutions can be improved by the administration of the 3% diquafosol sodium ophthalmic solution and the 0.1% sodium hyaluronate ophthalmic solution in combination. In other words, the administration of a $P2Y_2$ receptor agonist at a therapeutically effective concentration and hyaluronic acid or a salt thereof at a therapeutically effective concentration in combination is expected to have an excellent therapeutic effect on dry eye associated with severe corneal epithelial disorders.

[Pharmacological Test 3]

For the purpose of examining as to whether or not an increase in tear meniscus area values is observed when a $P2Y_2$ receptor agonist at a therapeutically effective concentration is combined with hyaluronic acid or a salt thereof at a concentration which is employed as an additive, the time course of a change in the tear meniscus area value after the sequential ocular instillation of the 3% diquafosol sodium and the 0.002% sodium hyaluronate was evaluated in the same manner as in Pharmacological test 1.

(Drug Preparation Method)

A 3% diquafosol sodium ophthalmic solution was prepared in the same manner as in the above-mentioned Pharmacological test 1. A 0.002% sodium hyaluronate ophthalmic solution was prepared by diluting "Hyalein® ophthalmic solution 0.3%" manufactured and sold by Santen Pharmaceutical Co., Ltd. with physiological saline.

(Test Method and Drug Administration Method)

With respect to normal male white rabbits (24 eyes of 12 rabbits in total), a photograph of a tear meniscus before the administration of a drug was taken in the same manner as in pharmacological test 1. Subsequently, the 3% diquafosol sodium ophthalmic solution and the 0.002% hyaluronic acid ophthalmic solution were administered in the following manner and a photograph of the tear meniscus was again taken 35 minutes after the administration.

Diquafosol single administration group: the 3% diquafosol sodium ophthalmic solution (50 µL) was instilled into eyes once (eight eyes of four rabbits per group).

Hyaluronic acid single administration group: the 0.002% sodium hyaluronate ophthalmic solution (50 µL) was instilled into eyes once (eight eyes of four rabbits per group).

Diquafosol/hyaluronic acid combination administration group: Five minutes after the instillation of the 3% diquafosol sodium ophthalmic solution (50 µL) into eyes, the 0.002% sodium hyaluronate ophthalmic solution (50 µL) was instilled into eyes (eight eyes of four rabbits per group).

(Results)

The change in the tear meniscus area before and after the administration of each of the drugs was calculated as a "Δ tear meniscus area value". The results are shown in Table 1.

TABLE 1

| Groups | Δ tear meniscus area value (mm²) |
|---|---|
| Hyaluronic acid single administration group | −0.497 |
| Diquafosol single administration group | 1.127 |
| Diquafosol/hyaluronic acid combination administration group | 0.928 |

(Discussion)

As apparent from Table 1, in the diquafosol/hyaluronic acid combination administration group, although an increase in the tear meniscus area values to a greater extent than that in hyaluronic acid single administration group was observed, the action was equal to or lower than that in diquafosol single administration group. In other words, it was demonstrated that the 0.002% sodium hyaluronate ophthalmic solution did not at all promote the tear secretion action of the 3% diquafosol sodium ophthalmic solution.

As mentioned above, it was demonstrated that a remarkable tear secretion promotion action is achieved when a $P2Y_2$ receptor agonist at a therapeutically effective concentration and hyaluronic acid or a salt thereof at a therapeutically effective concentration are administered in combination (see Pharmacological test 1), and that the action is not observed when the $P2Y_2$ receptor agonist at a therapeutically effective concentration and hyaluronic acid or a salt thereof at a concentration which is employed as an additive are administered in combination.

[Pharmacological Test 4]

The time course of a change in tear meniscus area values after the sequential instillation of 3% diquafosol sodium and 0.3% sodium hyaluronate into eyes was evaluated in the same manner as in Pharmacological test 1.

(Drug Reparation Method)

A 3% diquafosol sodium ophthalmic solution was prepared in the same manner as in the above-mentioned Pharmacological test 1. "Hyalein® ophthalmic solution 0.3%" manufactured and sold by Santen Pharmaceutical Co., Ltd. was used as a 0.3% sodium hyaluronate ophthalmic solution.

(Test Method and Drug Administration Method)

With respect to each of normal male white rabbits (18 eyes of 9 rabbits in total), a photograph of a tear meniscus was taken before the administration of each of the drug in the same manner as in Pharmacological test 1. Subsequently, the 3% diquafosol sodium ophthalmic solution and the 0.3% hyaluronic acid ophthalmic solution were administered in the following manner, and a photograph of the tear meniscus was taken again after 35 minutes.

- Diquafosol single administration group: the 3% diquafosol sodium ophthalmic solution (50 μL) was instilled into eyes once (6 eyes of three rabbits per group).
- Hyaluronic acid single administration group: the 0.3% sodium hyaluronate ophthalmic solution (50 μL) was instilled into eyes once (6 eyes of 3 rabbits per group).
- Diquafosol/hyaluronic acid combination administration group: Five minutes after the instillation of the 3% diquafosol sodium ophthalmic solution (50 μL) into eyes, the 0.3% sodium hyaluronate ophthalmic solution (50 μL) was instilled into eyes (6 eyes of 3 rabbits per group).

(Results)

The change in the tear meniscus area before and after the administration of each of the drugs was calculated as a "Δ tear meniscus area value". The results are shown in Table 2.

TABLE 2

| Groups | Δ tear meniscus area value (mm²) |
|---|---|
| Hyaluronic acid single administration group | 0.559 |
| Diquafosol single administration group | 1.434 |
| Diquafosol/hyaluronic acid combination administration group | 3.373 |

(Discussion)

As apparent from Table 2, in the diquafosol/hyaluronic acid combination administration group, a greatly higher effect than the sum total of the "Δ tear meniscus area value" observed in the hyaluronic acid single administration group or the diquafosol single administration group was confirmed. In other words, it was found that the 0.3% sodium hyaluronate ophthalmic solution can remarkably promote the tear secretion action of the 3% diquafosol sodium ophthalmic solution, as in the case of the 0.1% sodium hyaluronate ophthalmic solution.

As mentioned above, it was confirmed again that a remarkable tear secretion promotion action can be achieved when a $P2Y_2$ receptor agonist at a therapeutically effective concentration and hyaluronic acid or a salt thereof at a therapeutically effective concentration are administered in combination.

Preparation Examples

The drugs of the present invention will be described more specifically with reference to preparation examples. However, the present invention is not limited to the preparation examples.

Formulation Example 1

An Ophthalmic Solution (the Concentration of Diquafosol Sodium: 3% (w/v), the Concentration of Sodium Hyaluronate: 0.1% (w/v))

In 100 ml:

| | |
|---|---|
| diquafosol sodium | 3.0 g |
| sodium hyaluronate | 0.1 g |
| sodium chloride | 0.9 g |
| sodium hydrogen phosphate hydrate | q.s. |
| sterilized purified water | q.s. |

Diquafosol sodium, sodium hyaluronate and the other components are added to sterilized purified water, and the resultant mixture is fully mixed, thereby preparing an ophthalmic solution. An ophthalmic solution having a diquafosol sodium concentration of 0.5% (w/v), 1% (w/v) or 5% (w/v) and a sodium hyaluronate concentration of 0.3% (w/v) or 0.5% (w/v) can be prepared by varying the amounts of diquafosol sodium and sodium hyaluronate to be added.

Formulation Example 2

An Ophthalmic Ointment (the Concentration of Diquafosol Sodium: 3% (w/w), the Concentration of Sodium Hyaluronate: 0.1% (w/w))

In 100 g:

| | |
|---|---|
| diquafosol sodium | 3.0 g |
| sodium hyaluronate | 0.1 mg |
| liquid paraffin | 10 mg |
| white petrolatum | q.s. |

Diquafosol sodium and sodium hyaluronate are added to white petrolatum and liquid paraffin which are melted homogeneously and the resultant mixture is fully mixed and then cooled gradually, thereby preparing an ophthalmic ointment. An ophthalmic ointment having a diquafosol sodium concentration of 0.5% (w/v), 1% (w/v) or 5% (w/v) and a sodium hyaluronate concentration of 0.3% (w/v) or 0.5% (w/v) can be prepared by varying the amounts of diquafosol sodium and sodium hyaluronate to be added.

Industrial Applicability

An agent for treatment of dry eye characterized by comprising a combination of a $P2Y_2$ receptor agonist at a therapeutically effective concentration and hyaluronic acid or a salt thereof at a therapeutically effective concentration and having a dosage form of an ophthalmic agent can promote the secretion of tear remarkably and can improve corneal epithelial disorders remarkably, and therefore is expected to be a novel agent for treatment of dry eye.

The invention claimed is:

1. An ophthalmic solution for treating dry eye, characterized by comprising a combination of $P^1,P^4$-bis(5'-uridyl)tetraphosphate or a salt thereof at a concentration of 1 to 5% (w/v) and hyaluronic acid or a salt thereof at a concentration of 0.05 to 0.5% (w/v).

2. An ophthalmic solution for treating dry eye, characterized by comprising a combination of $P^1,P^4$-bis(5'-uridyl)tetraphosphate or a salt thereof at a concentration of 3% (w/v) and hyaluronic acid or a salt thereof at a concentration of 0.1 to 0.5% (w/v).

3. A method for treating dry eye, comprising administering $P^1,P^4$-bis(5'-uridyl)tetraphosphate or a salt thereof at a concentration of 1 to 5% (w/v) and hyaluronic acid or a salt thereof at a concentration of 0.05 to 0.5% (w/v) in combination to a patient in need thereof, wherein the dosage form is an ophthalmic solution.

4. A method for treating dry eye, comprising administering $P^1,P^4$-bis(5'-uridyl)tetraphosphate or a salt thereof at a concentration of 3% (w/v) and hyaluronic acid or a salt thereof at a concentration of 0.1 to 0.5% (w/v) in combination to a patient, wherein the dosage form is an ophthalmic solution.

5. A method for promoting tear secretion, comprising administering $P^1,P^4$-bis(5'-uridyl)tetraphosphate or a salt thereof at a concentration of 1 to 5% (w/v) and hyaluronic acid or a salt thereof at a concentration of 0.05 to 0.5% (w/v) in combination to a patient in need thereof having dry eye so as to promote tear secretion, wherein the dosage form is an ophthalmic solution.

6. The method of claim 5, comprising administering the $P^1,P^4$-bis(5'-uridyl)tetraphosphate or a salt thereof at a concentration of 3% (w/v) and the hyaluronic acid or a salt thereof at a concentration of 0.1 to 0.5% (w/v).

* * * * *